(12) United States Patent
Alverdy

(10) Patent No.: US 9,668,900 B2
(45) Date of Patent: Jun. 6, 2017

(54) BALLOON SYSTEM AND METHODS FOR TREATING OBESITY

(71) Applicant: ReShape Medical, Inc., San Clemente, CA (US)

(72) Inventor: John C. Alverdy, Glenview, IL (US)

(73) Assignee: ReShape Medical, Inc., San Clemente, CA (US)

( * ) Notice: Subject to any disclaimer, the term of this patent is extended or adjusted under 35 U.S.C. 154(b) by 0 days.

(21) Appl. No.: 14/286,847

(22) Filed: May 23, 2014

(65) Prior Publication Data

US 2014/0257358 A1     Sep. 11, 2014

Related U.S. Application Data

(63) Continuation of application No. 12/625,473, filed on Nov. 24, 2009, now Pat. No. 8,845,672, which is a continuation-in-part of application No. 12/257,724, filed on Oct. 24, 2008, now abandoned, which is a continuation-in-part of application No. 10/513,583, filed as application No. PCT/US03/12782 on Apr. 25, 2003, now abandoned.

(60) Provisional application No. 60/379,540, filed on May 9, 2002.

(51) Int. Cl.
*A61F 5/00* (2006.01)

(52) U.S. Cl.
CPC ............. *A61F 5/003* (2013.01); *A61F 5/004* (2013.01)

(58) Field of Classification Search
CPC .. A61F 5/003; A61F 5/0036; A61B 17/12136; A61M 25/10184

USPC ............ 606/192, 159, 191; 604/96.01, 909; 623/23.65, 23.67

See application file for complete search history.

(56) References Cited

U.S. PATENT DOCUMENTS

| | | | |
|---|---|---|---|
| 1,666,690 A | | 4/1928 | Drevitson |
| 1,690,995 A | * | 11/1928 | Pratt ..................... A61M 29/02 138/93 |
| 2,493,326 A | | 1/1950 | Trinder |
| 2,579,301 A | | 12/1951 | Buntin |
| 3,131,867 A | | 5/1964 | Miller et al. |
| 4,133,315 A | | 1/1979 | Berman et al. |
| 4,198,983 A | | 4/1980 | Becker et al. |

(Continued)

FOREIGN PATENT DOCUMENTS

| | | |
|---|---|---|
| CA | 2638988 | 5/2007 |
| DE | 8708978 U1 | 11/1987 |

(Continued)

OTHER PUBLICATIONS

European Search Report-Supplementary; EP 03726447.0, Applicant: Applied Medical Resources Corporation: Mar. 1, 2006, 3 pgs.

(Continued)

*Primary Examiner* — Julie A Szpira
(74) *Attorney, Agent, or Firm* — Perkins Coie LLP

(57) ABSTRACT

A medical system for the treatment of morbid obesity comprising an inflatable balloon implanted in a gastric cavity, a percutaneous fillant delivery tube and a control module connected to the tube for regulating the inflation and deflation of the balloon. The balloon may be individually contoured and inflated to occupy a large volume of the gastric cavity to provide a feeling of satiety. The balloon may also be deflated to give the gastric cavity lining a rest during less critical time.

8 Claims, 2 Drawing Sheets

(56) References Cited

U.S. PATENT DOCUMENTS

Figure 1:
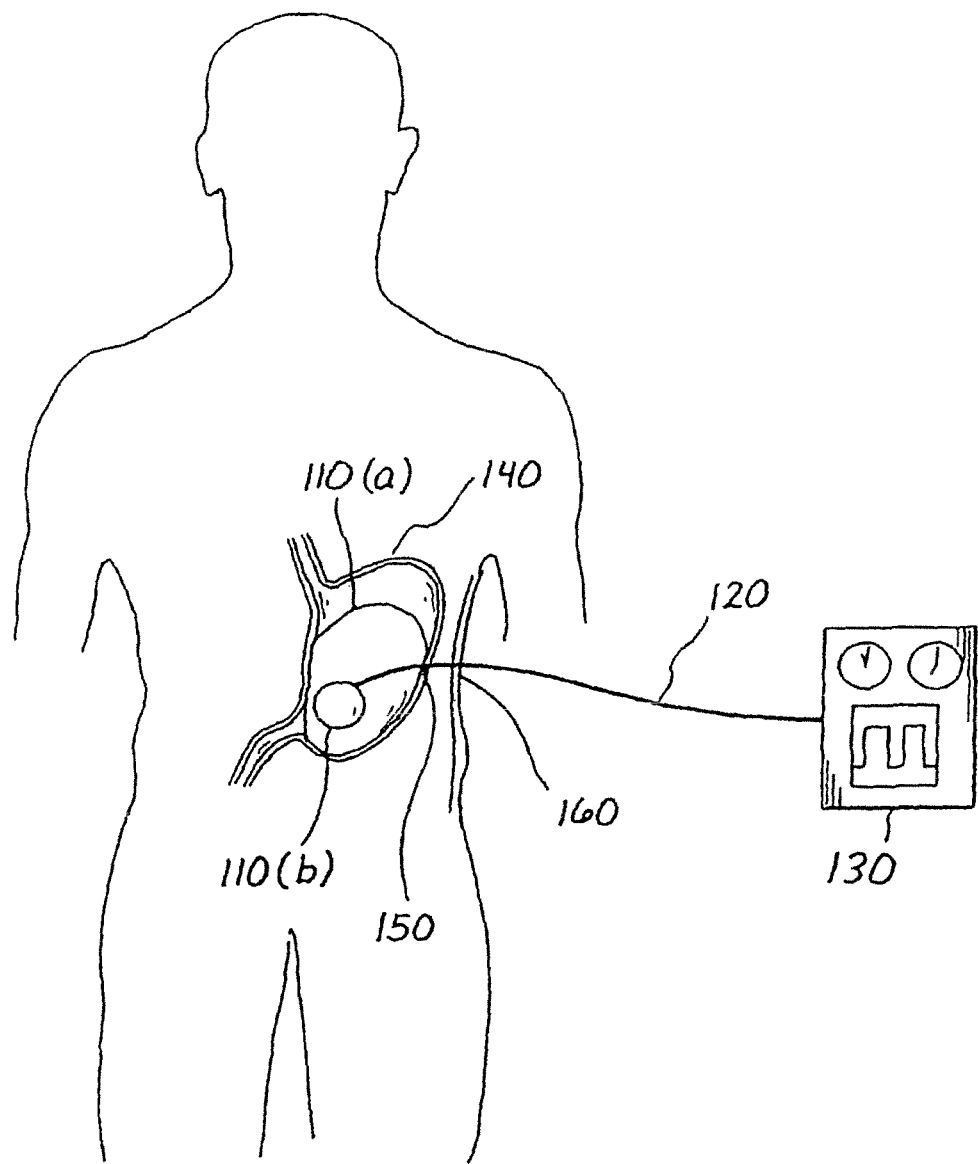

| | | |
|---|---|---|
| 4,246,893 A | 1/1981 | Berson |
| 4,356,824 A | 11/1982 | Vazquez |
| 4,368,739 A | 1/1983 | Nelson, Jr. |
| 4,416,267 A | 11/1983 | Garren et al. |
| 4,436,087 A | 3/1984 | Ouchi |
| 4,465,072 A | 8/1984 | Taheri |
| 4,465,818 A | 8/1984 | Shirahata et al. |
| 4,485,805 A | 12/1984 | Foster, Jr. |
| 4,543,089 A | 9/1985 | Moss |
| 4,598,699 A | 7/1986 | Garren et al. |
| 4,694,827 A | 9/1987 | Weiner et al. |
| 4,723,547 A | 2/1988 | Kullas et al. |
| 4,763,653 A | 8/1988 | Rockey |
| 4,899,747 A | 2/1990 | Garren et al. |
| 4,940,458 A | 7/1990 | Cohn |
| 5,073,347 A | 12/1991 | Garren et al. |
| 5,084,061 A | 1/1992 | Gau et al. |
| 5,123,840 A | 6/1992 | Nates |
| 5,224,626 A | 7/1993 | Hernandez |
| 5,234,454 A | 8/1993 | Bangs |
| 5,259,399 A * | 11/1993 | Brown .................. 128/897 |
| 5,263,934 A | 11/1993 | Haak |
| 5,273,536 A | 12/1993 | Savas |
| 5,318,530 A | 6/1994 | Nelson, Jr. |
| 5,334,187 A | 8/1994 | Fischell et al. |
| 5,431,173 A | 7/1995 | Chin et al. |
| 5,496,271 A | 3/1996 | Burton et al. |
| 5,516,812 A | 5/1996 | Chu et al. |
| 5,575,772 A | 11/1996 | Lennox |
| 5,639,810 A | 6/1997 | Smith, III et al. |
| 5,643,209 A | 7/1997 | Fugoso et al. |
| 5,713,486 A | 2/1998 | Beech |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,904,701 A | 5/1999 | Daneshvar |
| 5,938,669 A | 8/1999 | Klaiber et al. |
| 5,976,073 A | 11/1999 | Ouchi |
| 5,993,473 A * | 11/1999 | Chan .................. A61F 5/004 604/96.01 |
| 5,997,503 A | 12/1999 | Willis et al. |
| 6,050,274 A | 4/2000 | Gelardi et al. |
| 6,149,621 A | 11/2000 | Makihara |
| 6,179,878 B1 | 1/2001 | Duerig et al. |
| 6,254,355 B1 | 7/2001 | Gharib |
| 6,276,567 B1 | 8/2001 | Diaz et al. |
| 6,280,411 B1 | 8/2001 | Lennox |
| 6,283,951 B1 | 9/2001 | Flaherty et al. |
| 6,423,058 B1 | 7/2002 | Edwards et al. |
| 6,427,089 B1 | 7/2002 | Knowlton |
| 6,453,907 B1 | 9/2002 | Forsell |
| 6,454,785 B2 | 9/2002 | De Hoyos Garza |
| 6,524,234 B2 | 2/2003 | Ouchi |
| 6,535,764 B2 | 3/2003 | Imran et al. |
| 6,540,789 B1 | 4/2003 | Silverman et al. |
| 6,547,788 B1 | 4/2003 | Maguire et al. |
| 6,579,301 B1 | 6/2003 | Bales et al. |
| 6,592,552 B1 | 7/2003 | Schmidt |
| 6,613,018 B2 | 9/2003 | Bagga et al. |
| 6,613,037 B2 | 9/2003 | Khosravi et al. |
| 6,689,051 B2 | 2/2004 | Nakada et al. |
| 6,706,010 B1 | 3/2004 | Miki et al. |
| 6,746,460 B2 | 6/2004 | Gannoe et al. |
| 6,826,428 B1 | 11/2004 | Chen et al. |
| 6,850,128 B2 | 2/2005 | Park |
| 6,866,627 B2 | 3/2005 | Nozue |
| 6,866,657 B2 | 3/2005 | Shchervinsky |
| 6,869,431 B2 | 3/2005 | Maguire et al. |
| 6,890,300 B2 | 5/2005 | Lloyd et al. |
| 6,890,346 B2 | 5/2005 | Ganz et al. |
| 6,902,535 B2 | 6/2005 | Eberhart et al. |
| 6,923,754 B2 | 8/2005 | Lubock |
| 6,931,286 B2 | 8/2005 | Sigg et al. |
| 6,939,299 B1 | 9/2005 | Petersen et al. |
| 6,942,680 B2 | 9/2005 | Grayzel et al. |
| 6,958,052 B1 | 10/2005 | Charlton |
| 7,001,419 B2 | 2/2006 | DiCaprio et al. |
| 7,016,735 B2 | 3/2006 | Imran et al. |
| 7,020,531 B1 | 3/2006 | Colliou et al. |
| 7,033,373 B2 | 4/2006 | de la Torre et al. |
| 7,056,305 B2 | 6/2006 | Garza Alvarez |
| 7,076,305 B2 | 7/2006 | Imran et al. |
| 7,081,125 B2 | 7/2006 | Edwards et al. |
| 7,131,945 B2 | 11/2006 | Fink et al. |
| 7,483,746 B2 | 1/2009 | Lee et al. |
| 7,625,355 B2 | 12/2009 | Yu |
| 7,749,254 B2 | 7/2010 | Sobelman et al. |
| 7,828,749 B2 | 11/2010 | Douglas et al. |
| 7,829,572 B2 | 11/2010 | Didiuk et al. |
| 7,931,693 B2 | 4/2011 | Binmoeller |
| 8,083,757 B2 | 12/2011 | Gannoe et al. |
| 8,556,925 B2 | 10/2013 | Makower et al. |
| 8,840,952 B2 | 9/2014 | Ashby et al. |
| 8,894,568 B2 | 11/2014 | Pecor et al. |
| 9,050,174 B2 | 6/2015 | Pecor et al. |
| 9,149,611 B2 | 10/2015 | Bouasaysy et al. |
| 2001/0022988 A1 | 9/2001 | Schwarz et al. |
| 2001/0037127 A1 | 11/2001 | De Hoyos Garza |
| 2002/0055757 A1 | 5/2002 | Torre et al. |
| 2002/0107515 A1 | 8/2002 | Edwards et al. |
| 2002/0161388 A1 | 10/2002 | Samuels et al. |
| 2002/0173804 A1 | 11/2002 | Rousseau |
| 2003/0105800 A1 | 6/2003 | Cullen |
| 2003/0114878 A1 | 6/2003 | Diederich et al. |
| 2003/0171768 A1 | 9/2003 | McGhan |
| 2003/0187390 A1 | 10/2003 | Bates et al. |
| 2004/0044354 A1 | 3/2004 | Gannoe et al. |
| 2004/0059289 A1 | 3/2004 | Garza Alvarez |
| 2004/0059290 A1 | 3/2004 | Palasis |
| 2004/0073162 A1 | 4/2004 | Bleam et al. |
| 2004/0087902 A1 | 5/2004 | Richter |
| 2004/0093058 A1 | 5/2004 | Cottone et al. |
| 2004/0106899 A1 | 6/2004 | McMichael et al. |
| 2004/0116897 A1 | 6/2004 | Aboul-Hosn |
| 2004/0127915 A1 | 7/2004 | Fleenor et al. |
| 2004/0186502 A1 | 9/2004 | Sampson et al. |
| 2004/0186503 A1 | 9/2004 | Delegge |
| 2004/0220665 A1 | 11/2004 | Hossainy et al. |
| 2004/0236280 A1 | 11/2004 | Rice et al. |
| 2004/0236361 A1 | 11/2004 | Sakurai |
| 2004/0254600 A1 | 12/2004 | Zarbatany et al. |
| 2005/0027283 A1 | 2/2005 | Richard et al. |
| 2005/0027313 A1 | 2/2005 | Shaker |
| 2005/0038415 A1 | 2/2005 | Rohr et al. |
| 2005/0055039 A1 | 3/2005 | Burnett et al. |
| 2005/0059990 A1 | 3/2005 | Ayala et al. |
| 2005/0075624 A1 | 4/2005 | Miesel |
| 2005/0085792 A1 | 4/2005 | Gershowitz |
| 2005/0119674 A1 | 6/2005 | Gingras |
| 2005/0131442 A1 | 6/2005 | Yachia et al. |
| 2005/0143784 A1 | 6/2005 | Imran |
| 2005/0159769 A1 | 7/2005 | Alverdy |
| 2005/0177103 A1 | 8/2005 | Hunter et al. |
| 2005/0192614 A1 | 9/2005 | Binmoeller |
| 2005/0192615 A1 | 9/2005 | Torre et al. |
| 2005/0203563 A9 | 9/2005 | Pederson, Jr. et al. |
| 2005/0228504 A1 | 10/2005 | Demarais |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0058829 A1 | 3/2006 | Sampson et al. |
| 2006/0095032 A1 | 5/2006 | Jackson et al. |
| 2006/0142700 A1 | 6/2006 | Sobelman et al. |
| 2006/0178691 A1 | 8/2006 | Binmoeller |
| 2006/0184112 A1 | 8/2006 | Horn et al. |
| 2006/0235448 A1 | 10/2006 | Roslin et al. |
| 2006/0259020 A1 | 11/2006 | Sharratt |
| 2006/0270906 A1 | 11/2006 | Matsuno |
| 2006/0271088 A1 | 11/2006 | Alfrhan |
| 2007/0016262 A1 | 1/2007 | Gross et al. |
| 2007/0078476 A1 | 4/2007 | Hull et al. |
| 2007/0083224 A1 | 4/2007 | Hively |
| 2007/0093728 A1 | 4/2007 | Douglas et al. |

(56) References Cited

U.S. PATENT DOCUMENTS

| | | |
|---|---|---|
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0118168 A1 | 5/2007 | Lointier et al. |
| 2007/0135829 A1 | 6/2007 | Paganon et al. |
| 2007/0142770 A1 | 6/2007 | Rioux et al. |
| 2007/0149994 A1 | 6/2007 | Sosnowski et al. |
| 2007/0173881 A1 | 7/2007 | Birk et al. |
| 2007/0233161 A1 | 10/2007 | Weller et al. |
| 2007/0250020 A1 | 10/2007 | Kim et al. |
| 2007/0265369 A1 | 11/2007 | Muratoglu et al. |
| 2007/0265598 A1 | 11/2007 | Karasik |
| 2007/0288033 A1 | 12/2007 | Murature et al. |
| 2008/0058887 A1 | 3/2008 | Griffin et al. |
| 2008/0082056 A1 | 4/2008 | Mauch et al. |
| 2008/0097513 A1 | 4/2008 | Kaji et al. |
| 2008/0119729 A1 | 5/2008 | Copa et al. |
| 2008/0172079 A1 | 7/2008 | Birk |
| 2008/0190363 A1 | 8/2008 | Chen et al. |
| 2008/0208135 A1 | 8/2008 | Annunziata et al. |
| 2008/0208241 A1 | 8/2008 | Weiner et al. |
| 2008/0233167 A1 | 9/2008 | Li et al. |
| 2008/0243071 A1 | 10/2008 | Quijano et al. |
| 2008/0243166 A1 | 10/2008 | Paganon et al. |
| 2008/0255601 A1 | 10/2008 | Birk |
| 2008/0312679 A1 | 12/2008 | Hardert et al. |
| 2008/0319471 A1 | 12/2008 | Sosnowski et al. |
| 2009/0048624 A1 | 2/2009 | Alverdy |
| 2009/0259236 A2 | 10/2009 | Burnett et al. |
| 2009/0275973 A1 | 11/2009 | Chen et al. |
| 2009/0287231 A1 | 11/2009 | Brooks et al. |
| 2010/0023047 A1 | 1/2010 | Simpson |
| 2010/0049224 A1 | 2/2010 | Vargas |
| 2010/0063530 A1 | 3/2010 | Valencon |
| 2010/0130998 A1 | 5/2010 | Alverdy |
| 2010/0174307 A1 | 7/2010 | Birk |
| 2010/0191270 A1 | 7/2010 | Garza Alvarez |
| 2010/0234853 A1 | 9/2010 | Pecor et al. |
| 2010/0243135 A1 | 9/2010 | Pepper et al. |
| 2010/0251837 A1 | 10/2010 | Bouasaysy et al. |
| 2011/0172767 A1 | 7/2011 | Rathi et al. |
| 2011/0178544 A1 | 7/2011 | Sosnowski et al. |
| 2011/0276076 A1 | 11/2011 | Paganon |
| 2011/0295300 A1 | 12/2011 | Verd et al. |
| 2012/0191126 A1 | 7/2012 | Pecor et al. |
| 2012/0271336 A1 | 10/2012 | Hamman et al. |
| 2012/0271338 A1 | 10/2012 | Bouasaysy et al. |
| 2012/0289992 A1 | 11/2012 | Quijano et al. |
| 2013/0035710 A1 | 2/2013 | Bouasaysy et al. |
| 2013/0053880 A1 | 2/2013 | Bouasaysy et al. |
| 2013/0102876 A1 | 4/2013 | Limon et al. |
| 2013/0261654 A1 | 10/2013 | Bouasaysy et al. |
| 2013/0296914 A1 | 11/2013 | Quijano et al. |
| 2014/0031850 A1 | 1/2014 | Bouasaysy et al. |
| 2014/0371775 A1 | 12/2014 | Ashby et al. |
| 2015/0216529 A1 | 8/2015 | Kwok et al. |
| 2015/0238342 A1 | 8/2015 | Sosnowski et al. |
| 2015/0265811 A1 | 9/2015 | Pecor |
| 2015/0366691 A1 | 12/2015 | Bouasaysy |
| 2016/0008156 A1 | 1/2016 | Pecor et al. |

FOREIGN PATENT DOCUMENTS

| | | |
|---|---|---|
| EP | 0103481 | 3/1984 |
| EP | 0457456 | 11/1991 |
| EP | 0485903 | 5/1992 |
| EP | 1781183 | 5/2007 |
| FR | 2862525 | 5/2005 |
| FR | 2892297 | 4/2007 |
| GB | 2090747 A | 7/1982 |
| GB | 2139902 | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333886 | 12/2006 |
| JP | 2009285135 A | 12/2009 |
| JP | 2015154964 A | 8/2015 |
| JP | 2016127954 A | 7/2016 |
| WO | WO-8805671 A1 | 8/1988 |
| WO | 9000369 A1 | 1/1990 |
| WO | 9925418 A1 | 5/1999 |
| WO | WO-0141700 | 6/2001 |
| WO | WO-0166166 | 9/2001 |
| WO | WO-0240081 | 5/2002 |
| WO | WO-2005082296 A1 | 9/2005 |
| WO | WO-2005107641 A2 | 11/2005 |
| WO | WO-2005120363 A1 | 12/2005 |
| WO | WO-2006035446 | 4/2006 |
| WO | WO-2006056944 | 6/2006 |
| WO | WO-2006128978 | 12/2006 |
| WO | WO-2007027812 | 3/2007 |
| WO | WO-2007053556 | 5/2007 |
| WO | WO-2007053706 | 5/2007 |
| WO | WO-2007053707 | 5/2007 |
| WO | WO-2007075810 | 7/2007 |
| WO | WO-2008042819 | 4/2008 |
| WO | WO-2008121831 | 10/2008 |
| WO | WO-2009055386 | 4/2009 |
| WO | WO-2009112786 | 9/2009 |
| WO | WO-2010048021 | 4/2010 |
| WO | WO-2010115161 | 10/2010 |
| WO | WO-2011011629 | 1/2011 |
| WO | WO-2011011741 | 1/2011 |
| WO | WO-2011011743 | 1/2011 |
| WO | WO-2011024077 | 3/2011 |
| WO | WO-2011038270 | 3/2011 |
| WO | WO-2011097637 | 8/2011 |
| WO | WO-2011127205 | 10/2011 |
| WO | WO-2012048226 | 4/2012 |

OTHER PUBLICATIONS

Final Office Action; U.S. Appl. No. 11/694,536, Mailing Date Mar. 11, 2011, 13 pages.

Final Office Action; U.S. Appl. No. 11/768,152, Mailing Date Jan. 19, 2011, 13 pages.

International Search Report; International Application No. PCT/US2010/042948; Applicant: ReShape Medical, Inc., Mailing Date Apr. 1, 2011, 11 pages.

International Search Report; International Application No. PCT/US2010/043136; Applicant: ReShape Medical, Inc., Mailing Date Apr. 12, 2011, 9 pages.

International Search Report; International Application No. PCT/US2010/050260; Applicant: ReShape Medical, Inc., Mailing Date Jun. 17, 2011, 9 pages.

International Search Report; International Application No. PCT/US2011/026233; Applicant: ReShape Medical, Inc., Mailing Date Apr. 26, 2011, 9 pages.

International Search Report; International Application No. PCT/US2011/031463; Applicant: ReShape Medical, Inc., Mailing Date Jun. 27, 2011, 10 pages.

International Search Report; International Application No. PCT/US2003/012782; Applicant: Applied Medical Resources Corporation, dated Oct. 28, 2003, 7 pages.

International Search Report; International Application No. PCT/US2006/042336; Applicant: Abdominus, Inc., dated: Mar. 14, 2007, 9 pages.

International Search Report; International Application No. PCT/US2006/042710; Applicant: Abdominus, Inc. et al., dated: Mar. 15, 2007, 9 pages.

International Search Report; International Application No. PCT/US2006/042711; Applicant: Abdominus, Inc. et al, dated Mar. 16, 2007, 9 pages.

International Search Report; International Application No. PCT/US2006/048647; Applicant: Abdominus, Inc. et al., dated: May 22, 2007, 12 pages.

International Search Report; International Application No. PCT/US2008/058677; Applicant: ReShape Medical, Inc. et al., dated: Aug. 21, 2008, 12 pages.

(56) References Cited

OTHER PUBLICATIONS

International Search Report; International Application No. PCT/US2008/068058; Applicant: ReShape Medical, Inc. et al., dated: Nov. 19, 2008, 11 pages.
International Search Report; International Application No. PCT/US2010/029865; Applicant: ReShape Medical, Inc., dated: Jan. 5, 2011, 9 pages.
International Search Report; International Application No. PCT/US2011/024077; Applicant: ReShape Medical, Inc., dated: Apr. 6, 2011, 12 pages.
International Search Report; International Application No. PCT/US2011/024082; Applicant: ReShape Medical, Inc., dated: Apr. 6, 2011, 10 pages.
International Search Report; International Application No. PCT/US1155373; Applicant: ReShape Medical, Inc., dated: Jan. 20, 2012, 7 pages.
"Living with the BIB: BioEnterics Intragastric Balloon Program: Patient Information"; INAMED Health: Bioenterics Corporation, ECO-SBA-10434; dated Apr. 20, 2004 and May 14, 2005, located online at: www.sydneyobesity.com.au/pdf/M946-01.pdf; 10 pages.
Non-Final Office Action; U.S. Appl. No. 11/263,302; dated: Oct. 9, 2012, 6 pages.
Non-Final Office Action; U.S. Appl. No. 11/694,536; dated: Oct. 26, 2011, 13 pages.
Non-Final Office Action; U.S. Appl. No. 12/723,545; dated: Feb. 29, 2012, 10 pages.
Non-Final Office Action; U.S. Appl. No. 12/625,473; dated: Oct. 24, 2011, 18 pages.
Non-Final Office Action; U.S. Appl. No. 12/625,473; dated: Jul. 12, 2012, 10 pages.
Non-Final Office Action; U.S. Appl. No. 12/753,751; dated: Oct. 5, 2012, 8 pages.
Non-Final Office Action; U.S. Appl. No. 13/074,956; dated: Oct. 1, 2012, 8pages.
ReShape Inflatable Gastric Balloon Going on Trial as Weight Loss Option, MedGadget: Internet Journal of Emerging Medical Technologies. Feb. 4, 2010, 5 pages.
Wahlen CH et al. "The BioEnterics Intragastric Balloon: How to use it" Obesity Surgery 2001; 11:524-527.
European Supplementary Search Report; EP Application No. 10802994.3, Applicant: ReShape Medical, Inc., mailed Jun. 28, 2013, 8 pgs.
European Supplementary Search Report; EP Application No. 10802918.2, Applicant: ReShape Medical, Inc., mailed Jun. 5, 2013, 6 pgs.
Extended European Search Report; Application No. EP11766679.2, Applicant ReShape Medical, Inc., mailed Dec. 12, 2013, 6 pages.
Extended European Search Report; Application No. EP11748141.6, Applicant: Reshape Medical, Inc., mailed Feb. 25, 2014, 6 pages.
Notice of Allowance; U.S. Appl. No. 12/753,803, dated May 13, 2014, 18 pages.
Canadian Office Action; App. No. CA2638988, dated Mar. 6, 2014, 4 pages.
Notice of Allowance: U.S. Appl. No. 12/753,803, dated May 13, 2014, 18 pages.
Final Office Action; U.S. Appl. No. 13/858,767, Mailing Date May 22, 2103, 12 pages.
Extended European Search Report; Application EP11740536.5, Applicant: ReShape Medical, Inc., mailed Jul. 3, 2014, 8 pages.
Final Office Action; U.S. Appl. No. 13/556,032, mailed on Jan. 28, 2014, 8 pages.
Non-Final Office Action; U.S. Appl. No. 13/386,650, mailed on Jun. 3, 2014, 15 pages.
Ostrovsky, ReShape Inflatable Gastric Balloon going on Trial as Weight Loss Option; http://www.medgadget.com/2010/02/reshape_inflatable_gastric_balloon_system_going_on_trial_as_weight_loss_option.html Feb. 4, 2010, retrieved on Feb. 10, 2013.
Extended European Search Report; Application EP11831683.5, Applicant: Reshape Medical, Inc., mailed Jul. 3, 2014, 8 pages.
Extended European Search Report; Application No. EP6827098.3, Applicant: Reshape Medical, Corporation, mailed on Aug. 25, 2014, 3 pages.
Extended European Search Report; Application No. EP6827314.3, Applicant: ReShape Medical Corporation, mailed Aug. 1, 2014, 3 pages.
Extended European Search Report; Application No. EP6827313.5, Applicant: ReShape Medical Corporation, mailed Jul. 30, 2014, 5 pages.
Extended European Search Report; Application No. EP6847847.8, Applicant ReShape Medical Corporation, mailed Aug. 14, 2014, 5 pages.
Final Office Action; U.S. Appl. No. 13/858,767, mailed on May 30, 2014, 12 pages.
Non-Final Office Action; U.S. Appl. No. 13/386,638, mailed on Jun. 27, 2014, 12 pages.
Canadian 2nd Office Action Application No. CA 2680124, Applicant: Reshape Medical, Inc., mailed Jul. 9, 2015, 3 pages.
Canadian Office Action: Application No. CA 2680124, Applicant: Reshape Medical Corporation, mailed Nov. 4, 2014, 3 pages.
Canadian Office Action; Application No. 2691530, mailed Dec. 18, 2014, 4 pages.
Canadian Office Action; Application No. CA 2638163, Applicant: Reshape Medical Corporation, mailed Mar. 10, 2015, 4 pages.
Canadian Office Action; Application No. CA 2638988, Applicant Reshape Medical Corporation, mailed Dec. 22, 2014, 3 pages.
Canadian Office Action; Application No. CA 2638988, Applicant Reshape Medical Corporation, mailed Mar. 6, 2014, 4 pages.
Canadian Office Action; Application No. CA 2638989, Applicant: Reshape Medical Corporation, mailed May 22, 2013, 3 pages.
Canadian Office Action; Application No. CA 2484838, Applicant: Reshape Medical, Inc., mailed Nov. 13, 2009, 3 pages.
Canadian Office Action; Application No. CA 2484838, Applicant: Reshape Medical, Inc., mailed Sep. 24, 2010, 3 pages.
Canadian Office Action; Application No. CA 2638163, Applicant: Reshape Medical Corporation, mailed Jul. 17, 2013, 2 pages.
Canadian Office Action; Application No. CA 2638988, Applicant: Reshape Medical Corporation, mailed May 28, 2013, 3 pages.
Canadian Office Action; Application No. CA 2780085, Applicant: Reshape Medical, Inc., mailed Jul. 23, 2012, 2 pages.
European Examination Report; Application No. 03726447.0, Applicant: Applied Medical Resources Corporation: Oct. 26, 2007, 4 pages.
European Examination Report; Application No. 08771842.5, May 7, 2015, 5 pages.
European Examination Report; Application No. EP 06827313.5, Applicant: Reshape Medical Inc., mailed Jul. 13, 2015, 5 pages.
European Examination Report; Application No. EP 06847847.8, Applicant: Reshape Medical Inc., mailed Jul. 13, 2015, 4 pages.
European Examination Report; Application No. EP 10802918.2, Applicant: Reshape Medical Inc., mailed Dec. 17, 2014, 5 pages.
European Examination Report; Application No. EP 108029943, Applicant: Reshape Medical Inc., mailed Dec. 18, 2014, 4 pages.
European Supplementary Search Report; Application No. 08771842.5, Apr. 24, 2015, 3 pages.
Extended European Search Report; Application No. 08732989.2, Applicant: Reshape Medical, Inc., mailed Oct. 16, 2014, 7 pages.
Final Office Action for Japanese Application No. 2014-52972, Applicant: ReShape Medical, Inc., mailed on Oct. 9, 2015, 8 pages.
Japanese Final Office Action; Application No. JP2013-043712, mailed Nov. 15, 2013, 5 pages.
Japanese Office Action; Application No. 2013-142327, mailed May 29, 2014, 4 pages.
Japanese Office Action; Application No. 2013-532976; mailed Jun. 26, 2015, 10 pages.
Japanese Office Action; Application No. 2014-52972; mailed Feb. 25, 2015, 7 pages.
Japanese Office Action; Application No. JP2010-501261, mailed Sep. 7, 2012, 10 pages.
Japanese Office Action; Application No. JP2010-515040, mailed Jan. 7, 2013, 17 pages.
Japanese Office Action; Application No. JP2012-503759, mailed Mar. 24, 2014, 5 pages.

(56) References Cited

OTHER PUBLICATIONS

Japanese Office Action; Application No. JP2013-43712, mailed Jan. 8, 2015, 8 pages.
Japanese Office Action; Application. No. JP2013-043712, mailed Apr. 22, 2013, 5 pages.
Partial Supplementary European Search Report for European Application No. 11740535.7, Applicant: ReShape Medical, Inc., mailed Oct. 20, 2015, 7 pages.
Cronin, Carmel G. et al., "Normal small bowel wall characteristics on MR enterography," European Journal of Radiology 74(2):207-211, Aug. 2010.
Gray, Henry, Anatomy of the Human Body. Philadelphia: Lea & Febiger, 1918. Section XI Splanchnology, 2g. The Small Intestine. Bartleby.com, 2000. Web. URL: www.bartleby.com/107/248.html. Accessed: Oct. 26, 2015. 12 pages.
Canadian Office Action; Application No. CA 2638163, Applicant: Reshape Medical, Inc., mailed Dec. 8, 2015, 4 pages.
Extended European Search Report; Application No. EP 11748141.6, Applicant: Reshape Medical, Inc., mailed Feb. 25, 2014, 6 pages.
Chou, Chyuan et al., "Structural Effects On The Thermal Properties Of PDPS/PDMS Copolymers," Journal of Thermal Analysis, vol. 40, pp. 657-667, 1993.
European Search Report for European Application No. 11740535.7, Applicant: ReShape Medical, Inc., mailed Mar. 8, 2016, 14 pages.
Extended European Search Report; Application No. 15198773.2, Application ReShape Medical Corporation, mailed Jul. 15, 2016, 7 pages.
Japanese Office Action for Patent Application No. 2015-084207 dated Mar. 16, 2016, 4 pages.
European Examination Report; Application No. 11766679.2, Applicant: Reshape Medical Inc., mailed Dec. 1, 2016, 4 pages.
European Examination Report; Application No. 11748141.6, Applicant: Reshape Medical Inc., mailed Dec. 8, 2016, 3 pages.
Extended European Search Report; Application No. 16183882.6, Applicant: Reshape Medical Inc., mailed Feb. 17, 2017, 9 pages.
European Search Report; Application No. 15198773.2, Applicant: Reshape Medical Inc., mailed Mar. 21, 2017, 4 pages.
Partial Supplementary European Search Report; Application No. 10759514.2, Applicant: Reshape Medical Inc., mailed Mar. 27, 2017, 6 pages.
Extended European Search Report; Application No. 10802993.5, Applicant: ReShape Medical Inc., mailed Apr. 19, 2017, 9 pages.
European Search Report; Application No. 06827313.5, Applicant: Reshape Medical Inc., mailed Feb. 3, 2017, 5 pages.

* cited by examiner

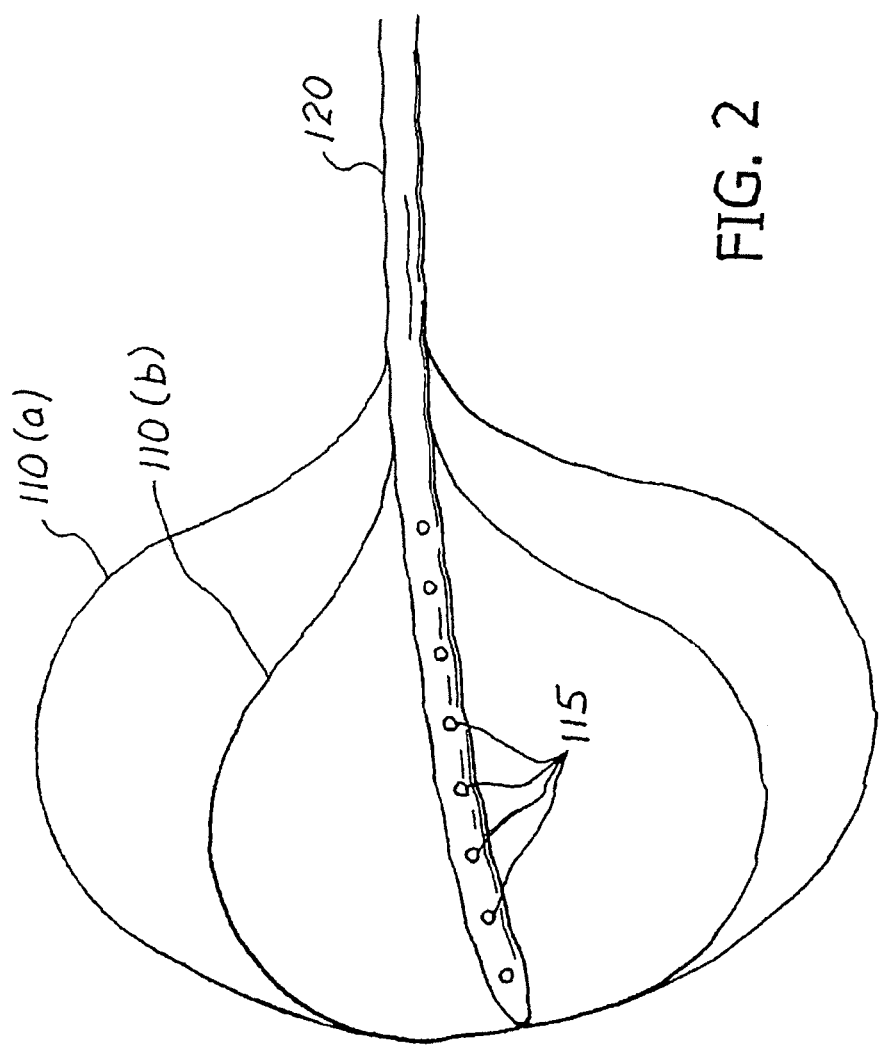

BALLOON SYSTEM AND METHODS FOR TREATING OBESITY

CROSS-REFERENCE TO RELATED APPLICATIONS

This application is a continuation of U.S. application Ser. No. 12/625,473, filed Nov. 24, 2009, now U.S. Pat. No. 8,845,672 whish is a continuation-in-part application of U.S. patent application Ser. No. 12/257,724, filed Oct. 24, 2008, now abandoned, which is a continuation-in-part of U.S. patent application Ser. No. 10/513,583, filed Nov. 2, 2004, now abandoned, which is a U.S. National Phase Application under 35 U.S.C. §371 of International Application No. PCT/US2003/012782, filed Apr. 25, 2003, which claims the benefit of U.S. Provisional Application No. 60/379,540, filed May 9, 2002. Each of the foregoing applications are incorporated herein by reference herein in their entireties.

BACKGROUND

Field

This invention generally relates to the treatment of morbid obesity and, more specifically, to a system and method for treating morbid obesity using a variably cycled percutaneous balloon implanted in the gastric cavity.

General Background

Morbid obesity is a major health problem confronting the general public and health care industry today. It is estimated that approximately 50% of the U.S. population is overweight and over ten million Americans are more than 100 pounds over their ideal weight. Generally, a person is considered morbidly (or seriously) obese if they are 100 pounds or more over their ideal weight. The morbidly obese group faces increased health risks including a higher likelihood of heart disease, hypertension, diabetes and certain cancers. Over 300,000 Americans die of obesity related illnesses each year. In addition, the morbidly obese generally have lower self-esteem and are more likely to suffer from depression than the general public.

Most obese individuals have struggled unsuccessfully with their weight for a lifetime. The numerous diets, behavioral therapy and treatments such as hypnosis, pituitary hormones and appetite suppressant drugs attest to the great difficulty many overweight people have in losing weight and keeping it off. Some of these weight loss strategies can be successful in the mildly obese people, but nearly all fail in individuals considered morbidly obese. These disappointing results have led many patients and their doctors to consider surgery as an option for weight loss.

Surgical techniques bring about weight loss primarily by limiting how much the stomach can hold. Today's most common surgical procedures to promote weight loss focus on decreasing food intake by restriction. Gastric banding, gastric bypass and vertical-banded gastroplasty are surgeries that limit the amount of food the stomach can hold by closing off or removing parts of the stomach. Other surgeries attempt to permanently fill the stomach with an inflated balloon. These treatments are invasive, require major surgery with hospitalization and are associated with complications.

The success rates of current treatments and procedures have been poor. With the restrictive procedure, the patient is usually limited to eating very small amounts of food at a time. For many people, this can create a "satisfied" feeling, but they often do not feel "full". The ability to eat a large amount of food at one time is lost; consequently, many patients return to eating excessive amounts of high calorie or high sugar liquid foods. Essentially, their diet includes milk shakes and ice cream.

As to the balloon procedure of the past, very limited positive results were achieved. The balloon was relatively small when compared to the overall volume of the morbidly obese stomach. This is due to physiological limitation on the balloon volume. That is, complications of the device precluded enlarging it to a volume that would occupy more of the stomach. Yet, in order for the balloon to achieve a patient's feeling of fullness and satiation, the balloon would need to occupy a large portion (volume) of the patient's stomach. A balloon occupying this much volume without fixation or an inflation/deflation cycling has the potential of blocking food flow and causing necrosis of the stomach wall, ulcers and/or bleeding.

Moreover, success depends on the ability of a treatment to "normalize" not only the mechanical and neurohormonal sensation of feeling full and satiated, but also involves psychological factors. Both the mechanical and neurohormonal factors relate to one's need to feel "full" and "satiated". Chemicals released by the stomach during the digestive process largely drive these factors. In other words, filling the stomach or limiting its pouch size controls these chemicals. Current surgical approaches, however, fail to achieve this global feeling of "satiety" response as they restrict food entry only into the small proximal stomach pouch and bypass the distal stomach where most of the neurohormonal chemical are normally released. Medical therapy is focused almost exclusively at the brain level and is likely to continue to fail as patients experience mood disorders and complications from medications. Accordingly, there is a need for a system and method for treating morbid obesity by restoring or normalizing the appropriate "fullness signals" from the stomach itself as this is the organ that regulates fullness. In particular, the system and method of the invention should cause a feeling of satiety from the stomach itself with less consumption of food by a morbidly obese patient.

SUMMARY

A system and method for treating morbid obesity using a variably cycled percutaneous balloon implanted in the gastric cavity to elicit signals directly from the entire stomach in order to cause a feeling of satiety with less food. This novel approach has the potential to offer a less invasive, more complete elicitation of the feeling of fullness in patients who chronically, and perhaps genetically overeat. The system of the invention includes a balloon device that is contoured to occupy the vast majority of the volume of the stomach. The system also has the capacity to automatically inflate and deflate the balloon, thereby avoiding the problem of pressure induced injury. With the advent of CT scanning and 3-dimensional imaging, patients may have balloons individually designed to meet the specific morphologic features of their stomachs. By fixation of the balloon device, the problems of migration and obstruction are avoided. Furthermore, the system and process of the invention apply appropriate inflation/deflation cycling with a computerized device so as to avoid complications of past devices.

These and other features and advantages of the invention will become more apparent with a discussion of preferred embodiments in reference to the associated drawings.

DRAWINGS

FIG. 1 illustrates a schematic view of a variably cycled percutaneous balloon placed within the gastric cavity of an individual in accordance with an embodiment of the invention; and FIG. 2 illustrates a cross-sectional view of an inflatable balloon and a fillant delivery tube according to the present invention.

DETAILED DESCRIPTION

With reference to FIGS. 1 and 2, a variably cycled percutaneous balloon system 100 for treating morbid obesity is illustrated and comprises an inflatable balloon no individually contoured to each patient's stomach, a percutaneous inflation or fillant delivery tube 120 having a proximal end and a distal end connected to the balloon no, and a control module 130 connected to the proximal end of the tube 120. The tube 120 includes at least one opening 115 for filling the balloon 110 with a biocompatible fillant. The control module 130 variably controls the inflation and deflation of the balloon no with the biocompatible fillant such as a liquid, gas, gel or a mixture thereof. In accordance with the teachings of the present invention, the tube 120 is passed through and affixed to abdominal wall 160 and stomach wall 150. The balloon no is then positioned into the stomach or gastric cavity 140. The positioning of the balloon 110 may be done, e.g., by the percutaneous endoscopic gastrostomy (PEG) technique, which is known in the art. The balloon no and tube 120 may be separate or integral components that are constructed from any surgical grade material. For example, the balloon no may be made from latex rubber which expands upon introduction of a fillant, and the tube 120 may be constructed of a metal or plastic material. The tube 120 is connected to the control module 130, which may be a fixed unit or a portable unit mounted to the patient's side. The control module 130 may be a personal computer such as a desktop computer, a laptop computer or a handheld computer. The control module 130 further includes a device such as a pump for introducing and removing a fillant to and from the balloon no.

A novel feature of the system 100 is it variably controls the inflation and deflation of the balloon no. For example, the system 100 may inflate and deflate the balloon no throughout a predetermined period of time such as a 24-hour period. The balloon no would occupy a large volume of the stomach 140 (as shown by reference number 110(a)) when it would be most beneficial for weight loss, and deflate to give the stomach lining a rest (as shown by reference number 110(b)) during less critical time, e.g., during sleeping time. Furthermore, an algorithm tailored to each patient's needs and programmed into the control module 130 is used to control the balloon size to minimize the desire to eat and to prevent blockage or stomach lining necrosis. Unlike the restrictive procedures of the prior art, the variable inflated balloon no would not limit nutrient absorption and not lead to altered food choices. This is achieved as the balloon no contacts a major portion of the stomach wall 150 when the balloon no is fully inflated. Thus, the system 100 of the invention creates a feeling of fullness and satiation by balancing the physiological, neurohormonal and chemical factors.

It will be understood that many modifications can be made to the disclosed embodiments without departing from the spirit and scope of the invention. As such, the above description should not be construed as limiting the invention, but should be interpreted as merely exemplary of preferred embodiments.

The invention claimed is:

1. A gastric device, comprising:
   an inflatable balloon, wherein the inflatable balloon is sized to make contact with a portion of a wall of a stomach of a human patient when the balloon is in an inflated state such that an outer surface of the balloon is configured to contact an inner surface of the wall;
   a fillant delivery tube extending through the inflatable balloon, wherein a proximal outer surface of the fillant delivery tube is directly connected to a first portion of the inflatable balloon and a distal outer surface of the fillant delivery tube is directly connected to a second portion of the inflatable balloon spaced apart from the first portion; and
   a control module for automatically inflating the balloon in the stomach with a biocompatible fillant,
   wherein the gastric device is configured to be inflated to a predetermined size with a predetermined volume of the biocompatible fillant.

2. The gastric device of claim 1 wherein the inflatable balloon is further sized to make contact with a major portion of a body of the stomach.

3. The gastric device of claim 1 wherein the control module further comprises a pump configured to introduce the fillant to the balloon.

4. The gastric device of claim 1 wherein the control module further comprises a pump configured to remove the fillant from the balloon.

5. A gastric device, comprising:
   an inflatable balloon;
   a fillant delivery tube extending through the inflatable balloon, wherein a proximal outer surface of the fillant delivery tube is directly connected to a first portion of the inflatable balloon and a distal outer surface of the fillant delivery tube is directly connected to a second portion of the inflatable balloon spaced apart from the first portion, and wherein a biocompatible fillant is transferred to the inflatable balloon via the fillant delivery tube; and
   means for automatically inflating the balloon in a stomach of a human patient with a biocompatible fillant, wherein the gastric device is configured to be inflated to a predetermined size with a predetermined volume of the biocompatible fillant, and
   wherein the inflatable balloon is sized to make contact with a portion of a wall of the stomach when the balloon is in an inflated state such that an outer surface of the balloon is configured to contact an inner surface of the wall.

6. The gastric device of claim 5 wherein the balloon is sized to make contact with a major portion of the wall of the stomach when the balloon is in an inflated state.

7. The gastric device of claim 5 wherein the means for automatically inflating the balloon comprises a pump.

8. The gastric device of claim 5 wherein the means for automatically inflating the balloon comprises an external control module, and wherein the external control module is connected to a proximal end of the fillant delivery tube.

* * * * *